US007248703B1

(12) United States Patent
Heine et al.

(10) Patent No.: US 7,248,703 B1
(45) Date of Patent: Jul. 24, 2007

(54) SYSTEMS AND METHODS FOR ADAPTIVE NOISE CANCELLATION

(75) Inventors: John C. Heine, Weston, MA (US); Istvan L. Ver, Stow, MA (US); William B. Coney, Littleton, MA (US); Robert D. Preuss, Sagamore Beach, MA (US)

(73) Assignee: BBN Technologies Corp., Cambridge, MA (US)

( * ) Notice: Subject to any disclaimer, the term of this patent is extended or adjusted under 35 U.S.C. 154(b) by 787 days.

(21) Appl. No.: 10/171,293

(22) Filed: Jun. 13, 2002

Related U.S. Application Data

(60) Provisional application No. 60/306,624, filed on Jul. 19, 2001, provisional application No. 60/301,104, filed on Jun. 26, 2001.

(51) Int. Cl.
*A61F 11/06* (2006.01)
*H04R 25/00* (2006.01)
*G10K 13/00* (2006.01)
*G10K 11/16* (2006.01)

(52) U.S. Cl. ................. 381/71.1; 381/94.1; 381/71.11; 381/71.12; 381/189; 181/296; 181/158

(58) Field of Classification Search ............... 381/71.1, 381/94.1, 71.11, 71.12, 189, 359; 181/296, 181/158; 367/901
See application file for complete search history.

(56) References Cited

U.S. PATENT DOCUMENTS 1,345,717 A 7/1920 Thomas
2,200,097 A 5/1940 Phelps
2,307,792 A 1/1943 Hoover, Jr.
2,325,424 A 7/1943 Rettinger
2,411,117 A 11/1946 Scherbatskoy
2,417,077 A 3/1947 Hoover, Jr.
2,520,706 A * 8/1950 Anderson et al. ........... 181/242
2,645,123 A 7/1953 Hundstad
2,772,746 A 12/1956 Merten
2,776,010 A 1/1957 Rike (Continued)

FOREIGN PATENT DOCUMENTS

JP 359217122 A 12/1984

OTHER PUBLICATIONS

Shust, Michael R. Electronic Removal of Outdoor Microphone Wind Noise. Acoustical Society of Americal. Presented Oct. 13, 1998. Published Jan. 11, 2002.*

(Continued)

*Primary Examiner*—Vivian Chin
*Assistant Examiner*—Devona E. Faulk
(74) *Attorney, Agent, or Firm*—Fish & Neave IP Group Ropes & Gray LLP

(57) ABSTRACT

A system (400) for reducing non-acoustic noise includes a primary sensor (420), at least one secondary sensor (410), a filter (415), and a summation unit (425). The primary sensor (420) measures pressure and produces a primary pressure signal. The at least one secondary sensor (410) measures pressure and produce a secondary pressure signal. The filter (415) processes the secondary pressure signal to produce a filtered pressure signal. The summation unit (425) subtracts the filtered pressure signal from the primary pressure signal to reduce non-acoustic noise in the primary pressure signal.

21 Claims, 6 Drawing Sheets

U.S. PATENT DOCUMENTS

| | | | | | |
|---|---|---|---|---|---|
| 3,067,404 | A | | 12/1962 | Hildebrandt | |
| 3,154,171 | A | | 10/1964 | Knutson et al. | 181/31 |
| 3,476,208 | A | | 11/1969 | Sellman et al. | 181/5 |
| 3,479,886 | A | | 11/1969 | Canfield | |
| 3,550,720 | A | * | 12/1970 | Ballard et al. | 181/175 |
| 3,572,462 | A | | 3/1971 | Gray | |
| 3,953,829 | A | | 4/1976 | Boyle | |
| 3,992,951 | A | | 11/1976 | Erspamer et al. | |
| 4,020,919 | A | | 5/1977 | Broding | |
| 4,065,648 | A | | 12/1977 | Cvetko et al. | |
| 4,153,815 | A | | 5/1979 | Chaplin et al. | 179/1 |
| 4,159,464 | A | | 6/1979 | Hall, Jr. | |
| 4,352,254 | A | | 10/1982 | Peter et al. | |
| 4,382,201 | A | | 5/1983 | Trzaskos | |
| 4,570,746 | A | * | 2/1986 | Das et al. | 381/359 |
| 4,600,077 | A | | 7/1986 | Drever | |
| 4,625,827 | A | | 12/1986 | Bartlett | |
| 4,692,912 | A | | 9/1987 | Mueller et al. | |
| 4,750,157 | A | | 6/1988 | Shei | |
| 4,764,908 | A | | 8/1988 | Greer, Jr. | |
| 4,899,845 | A | | 2/1990 | Bosco et al. | |
| 5,010,531 | A | | 4/1991 | McNeel | |
| 5,150,104 | A | | 9/1992 | Thomas et al. | |
| 5,231,252 | A | | 7/1993 | Sansone | |
| 5,288,955 | A | | 2/1994 | Staple et al. | |
| 5,339,287 | A | | 8/1994 | Bauer | 367/140 |
| 5,339,292 | A | | 8/1994 | Brown et al. | |
| 5,343,744 | A | | 9/1994 | Ammann | |
| 5,398,035 | A | | 3/1995 | Densmore et al. | |
| 5,435,178 | A | | 7/1995 | Edwards | |
| 5,444,790 | A | | 8/1995 | Kogen | |
| 5,457,995 | A | | 10/1995 | Staton et al. | |
| 5,469,408 | A | | 11/1995 | Woo | |
| 5,473,702 | A | * | 12/1995 | Yoshida et al. | 381/94.7 |
| 5,477,506 | A | | 12/1995 | Allen | 367/140 |
| 5,684,756 | A | * | 11/1997 | Schmitz et al. | 367/188 |
| 5,808,243 | A | * | 9/1998 | McCormick et al. | 181/5 |
| 5,917,921 | A | * | 6/1999 | Sasaki et al. | 381/94.1 |
| 5,929,754 | A | | 7/1999 | Park et al. | |
| 5,978,317 | A | | 11/1999 | Whitener | |
| 5,996,441 | A | | 12/1999 | Bateman | |
| 6,320,968 | B1 | | 11/2001 | Linder | 381/94.7 |
| 6,393,913 | B1 | | 5/2002 | Dyck et al. | |
| 6,502,459 | B1 | | 1/2003 | Bonne et al. | |
| 6,507,790 | B1 | * | 1/2003 | Radomski | 702/39 |
| 6,538,612 | B1 | | 3/2003 | King | |
| 6,604,432 | B1 | | 8/2003 | Hamblen et al. | |
| 6,609,069 | B2 | | 8/2003 | Gysling | |
| 6,805,008 | B2 | | 10/2004 | Selvakumar et al. | |
| 6,854,330 | B2 | | 2/2005 | Potter | |
| 6,935,458 | B2 | | 8/2005 | Owens | |
| 6,963,649 | B2 | * | 11/2005 | Vaudrey et al. | 381/94.7 |
| 6,978,673 | B2 | | 12/2005 | Johnson et al. | |
| 2002/0104379 | A1 | | 8/2002 | Ried et al. | |
| 2003/0179103 | A1 | | 9/2003 | Kamata | |
| 2005/0171710 | A1 | | 8/2005 | Gysling et al. | |
| 2006/0013425 | A1 | | 1/2006 | Kargus et al. | |

OTHER PUBLICATIONS

Bleaxzy, John C. Experimental Determination of the Effecitveness of Microphone Wind Screens. journal of the Audio Engineering Society. Jan. 1961, vol. 9, pp. 48-54.*

Beranek, Leo L. Acoustical Measurements. Published for the Acoustical Society of America by the American Institute of Physics. 1988 Edition. pp. 258-263.*

William B. Coney et al.; A Semi-Empirical Approach for Modeling Greenhouse Surface Wind Noise; SAE Technical Paper Series; May 17-20, 1999; pp. 1-9.

L. Beranek, Acoustical Measurements, published for the Acoustical Society of America by the American Institute of Physics, Revised Edition, pp. 258-263.

J. Bleazey, "Experimental Determination of the Effectiveness of Microphone Wind Screens", Journal of the Audio Engineering Society, vol. 9, No. 1, Jan. 1961, pp. 48-54.

W. Neise, "Theoretical and Experimental Investigations of Microphone Probes for Sound Measurements in Turbulent Flow", Journal of Sound and Vibration, 39(3), 1975, pp. 371-400.

M. Shust et al., "Electronic Removal of Outdoor Microphone Wind Noise", Acoustical Society of America 136$^{th}$ Meeting Lay Language Papers, Norfolk, VA, Oct. 1998, pp. 1-5.

* cited by examiner

SYSTEMS AND METHODS FOR ADAPTIVE NOISE CANCELLATION

CROSS REFERENCE TO RELATED APPLICATIONS

The instant application claims priority from provisional application No. 60/301,104, filed Jun. 26, 2001, and provisional application No. 60/306,624, filed Jul. 19, 2001, the disclosures of which are incorporated by reference herein in their entirety.

The instant application is related to co-pending application Ser. No. 10/170,865, entitled "Systems and Methods for Adaptive Wind Noise Rejection" and filed on Jun. 13, 2002, the disclosure of which is incorporated by reference herein.

FIELD OF THE INVENTION

The present invention relates generally to systems and methods for acoustic detection and, more particularly, to systems and methods for canceling noise in acoustic detection systems.

BACKGROUND OF THE INVENTION

A number of conventional systems detect, classify, and track air and ground bodies or targets. The sensing elements that permit these systems to perform these functions typically include arrays of microphones whose outputs are processed to reject coherent interfering acoustic noise sources (such as nearby machinery). Other sources of system noise include general acoustic background noise (e.g., leaf rustling) and wind noise. Both of these sources are uncorrelated between microphones. They can, however, be of sufficient magnitude to significantly impact system performance.

While uncorrelated noise is addressed by spatial array processing, there are limits to signal-to-noise improvements that can be achieved, usually on the order of 10*log N, where N is the number of microphones. Since ambient acoustic noise is scenario dependent, it can only be minimized by finding the quietest array location. At low wind speeds, system performance will be limited by ambient acoustic noise. However, at some wind speed, wind noise will become the dominant noise source—for typical scenarios at approximately 5 mph at low frequencies. The primary source of wind noise is the fluctuating, non-acoustic pressure due to the turbulent boundary layer induced by the presence of the sensor in the wind flow field. The impact of an increase in wind noise is a reduction in all aspects of system performance: detection range, probability of correct classification, and bearing estimation. For example, detection range can be reduced by a factor of two for each 3–6 dB increase in wind noise (depending on acoustic propagation conditions).

Therefore, there exists a need for systems and methods that can cancel wind noise so as to improve the performance of acoustic detection systems such as, for example, acoustic detection systems employed in vehicle mounted systems for which the effective wind speed includes the relative velocity of the vehicle when the vehicle is in motion.

SUMMARY OF THE INVENTION

Systems and methods consistent with the present invention address this and other needs by providing a multi-sensor windscreen assembly, and associated wind noise cancellation circuitry, to enable the detection of a desired acoustic signal while reducing wind noise. Multiple reference sensors, consistent with the present invention, may be distributed across a surface of a three dimensional body, such as a sphere, cylinder, or cone and may produce a response signal that corresponds to a net pressure acting on the three dimensional body. A primary sensor may further be located within the three dimensional body to sense acoustic pressure signals and non-acoustic pressure disturbances (e.g., wind noise). A finite impulse response (FIR) filter may adaptively filter the response signal from the multiple reference sensors to produce a filtered response. The filtered response may, in turn, be subtracted from a signal from the primary sensor to produce a signal that contains reduced non-acoustic disturbances. The filter may employ a least-means-square (LMS) algorithm for adjusting coefficients of the FIR filter to reduce the non-acoustic pressure disturbances. Systems and methods consistent with the present invention, thus, using an adaptive filtering algorithm, cancel wind noise from an acoustic signal so as to improve the performance of acoustic detection systems.

In accordance with the purpose of the invention as embodied and broadly described herein, a method for reducing non-acoustic noise includes measuring pressure at a primary sensor to produce a primary pressure signal; measuring pressure at least one secondary sensor to produce a secondary pressure signal; filtering the secondary pressure signal to produce a filtered pressure signal; and subtracting the filtered pressure signal from the primary pressure signal to reduce non-acoustic noise in the primary pressure signal.

In another implementation consistent with the present invention, a method of measuring fluid pressure includes measuring fluid pressure inside a windscreen to produce a measurement signal; inferring a net fluid pressure acting on the windscreen, the net fluid pressure comprising acoustic and non-acoustic pressure; estimating a component of the non-acoustic pressure that is correlated with the net fluid pressure; and eliminating the estimated component of non-acoustic pressure from the measurement signal.

In yet another implementation consistent with the present invention, a method for canceling disturbances from a sensor signal includes sensing disturbances at first and second sensors, the first sensor producing a first signal and the second sensor producing a second signal; adaptively filtering the first signal to produce a filtered signal; and subtracting the filtered signal from the second signal to cancel the disturbances from the second signal.

In a further implementation consistent with the present invention, a windscreen includes a three dimensional body comprising at least one surface; a first sensor located within the three dimensional body; and a plurality of second sensors distributed on the at least one surface of the body, the sensors configured to sense forces acting upon the body.

BRIEF DESCRIPTION OF THE DRAWINGS

The accompanying drawings, which are incorporated in and constitute a part of this specification, illustrate embodiments of the invention and, together with the description, explain the invention. In the drawings.

DETAILED DESCRIPTION

The following detailed description of the invention refers to the accompanying drawings. The same reference numbers in different drawings may identify the same or similar elements. Also, the following detailed description does not limit the invention. Instead, the scope of the invention is defined by the appended claims.

Systems and methods, consistent with the present invention, provide mechanisms that adaptively reduce noise in multiple signals received from a multi-sensor device. Multiple reference sensors, consistent with the present invention, may be distributed across a surface of a three dimensional body, such as a sphere, cylinder, or cone. A primary sensor may be located within the three dimensional body. Fluid pressures acting on the reference sensors may be combined to infer a net pressure acting on the three dimensional body, with the net pressure being correlated with the non-acoustic pressure acting over the entire three dimensional body. The net pressure acting on the three-dimensional windscreen is the source of the non-acoustic pressure acting on the primary sensor at a reduced level inside of the windscreen. The reference sensors may measure the acoustic signal, together with the non-acoustic wind pressure, and the reference sensor measurements may be passed through noise cancellation circuitry that estimates a component of the wind noise that is correlated with the primary sensor output. This correlated component may be subtracted from the primary sensor output to provide a reduced noise sensor output. The noise cancellation circuitry may include a finite impulse response (FIR) filter whose parameters are adaptively adjusted using a least-means-square (LMS) algorithm.

Exemplary Multi-Sensor Assembly

Figure 1:
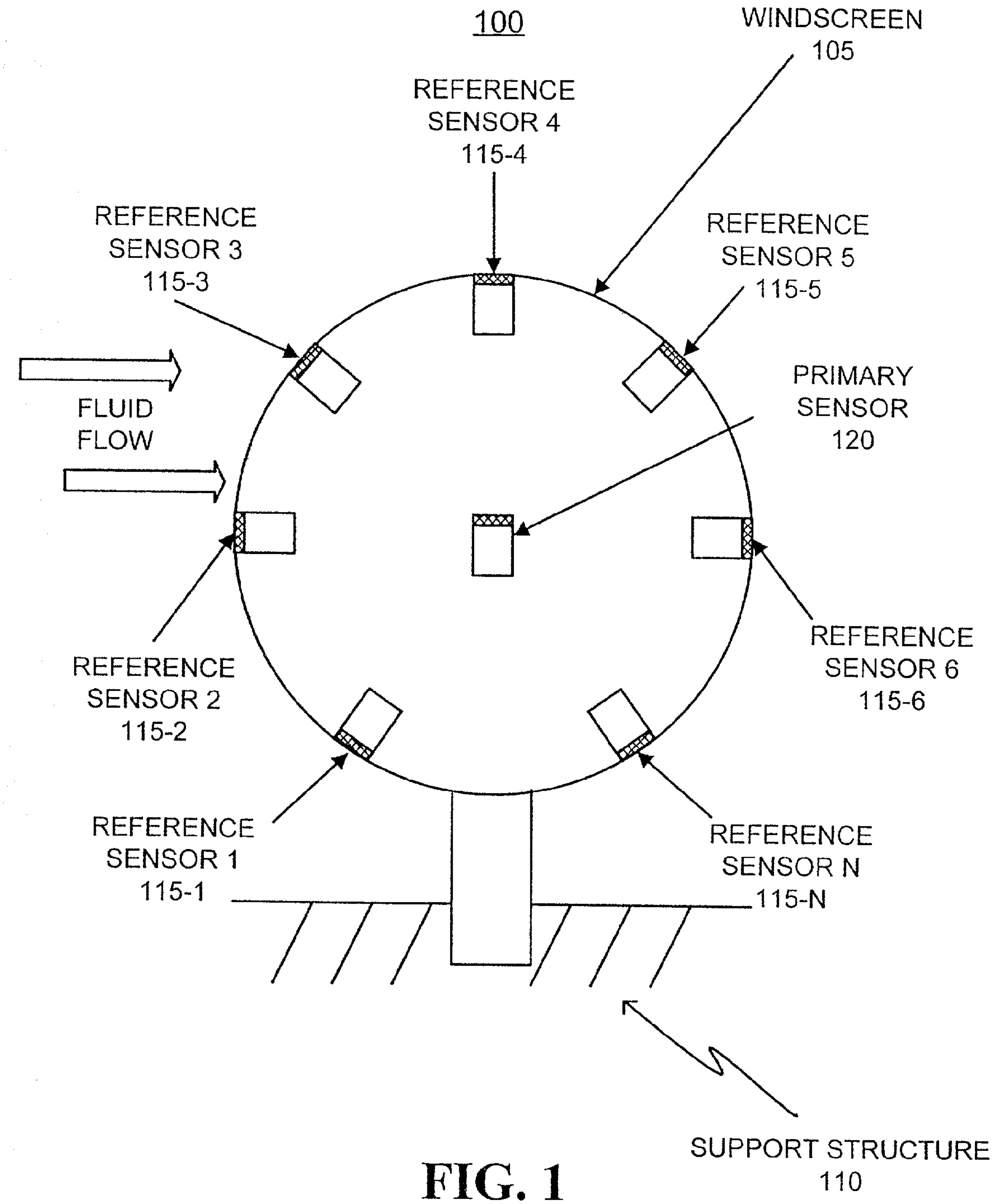
FIG. 1 illustrates an exemplary multi-sensor assembly consistent with the present invention.

FIG. 1 illustrates an exemplary multi-sensor assembly 100 consistent with the present invention. Multi-sensor assembly 100 may include a windscreen 105 coupled to a support structure 110. As illustrated, windscreen 105 may be configured as a three dimensional sphere. Windscreen 105 may, alternatively, be configured as a three dimensional cylinder, cone, or other shape (not shown). Windscreen 105 may further be constructed of a rigid or semi-rigid material. Windscreen 105 may also be constructed of a permeable or non-permeable material. For example, windscreen 105 may be constructed of foam and, thus, would be semi-rigid and permeable to fluids such as air or water.

Figure 2:
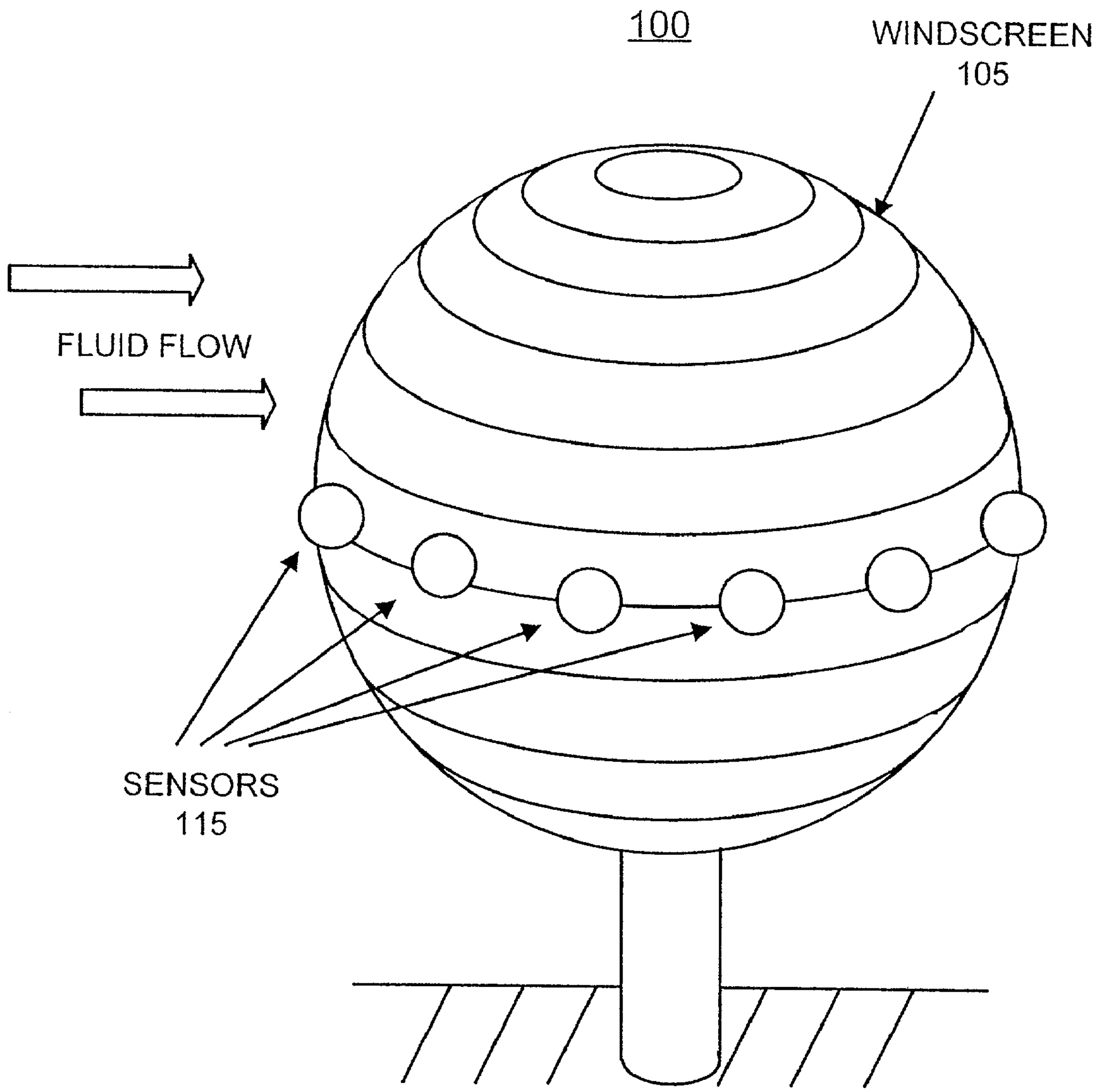
FIG. 2 illustrates an exemplary multi-sensor assembly with a spherical windscreen and equatorially distributed sensors consistent with the present invention.

As shown in FIG. 1, multiple reference sensors (reference sensor 1 115-1 through reference sensor N 115-N) may be distributed on a surface of windscreen 105. As further illustrated in FIG. 2, the multiple sensors may be distributed around an equator of spherical windscreen 105. One skilled in the art will recognize, also, that other sensor distributions may be possible. For example, sensors may be distributed at icoshedral points (not shown) on the surface of spherical windscreen 105. Distribution of the sensors across a surface of windscreen 105 can depend on the shape of the windscreen (e.g., spherical, cylindrical, conical) and the particular airflow anticipated upon the windscreen. Multi-sensor assembly 100 may additionally include a primary sensor 120 (FIG. 1) positioned within the approximate center of windscreen 105.

Each of the multiple reference sensors 115 may include any type of conventional transducer for measuring force or pressure. A piezoelectric transducer (e.g., a microphone) is one example of such a conventional transducer. In some embodiments of the invention, each of the multiple reference sensors 115 may measure acoustic and non-acoustic air pressure.

Figure 3:
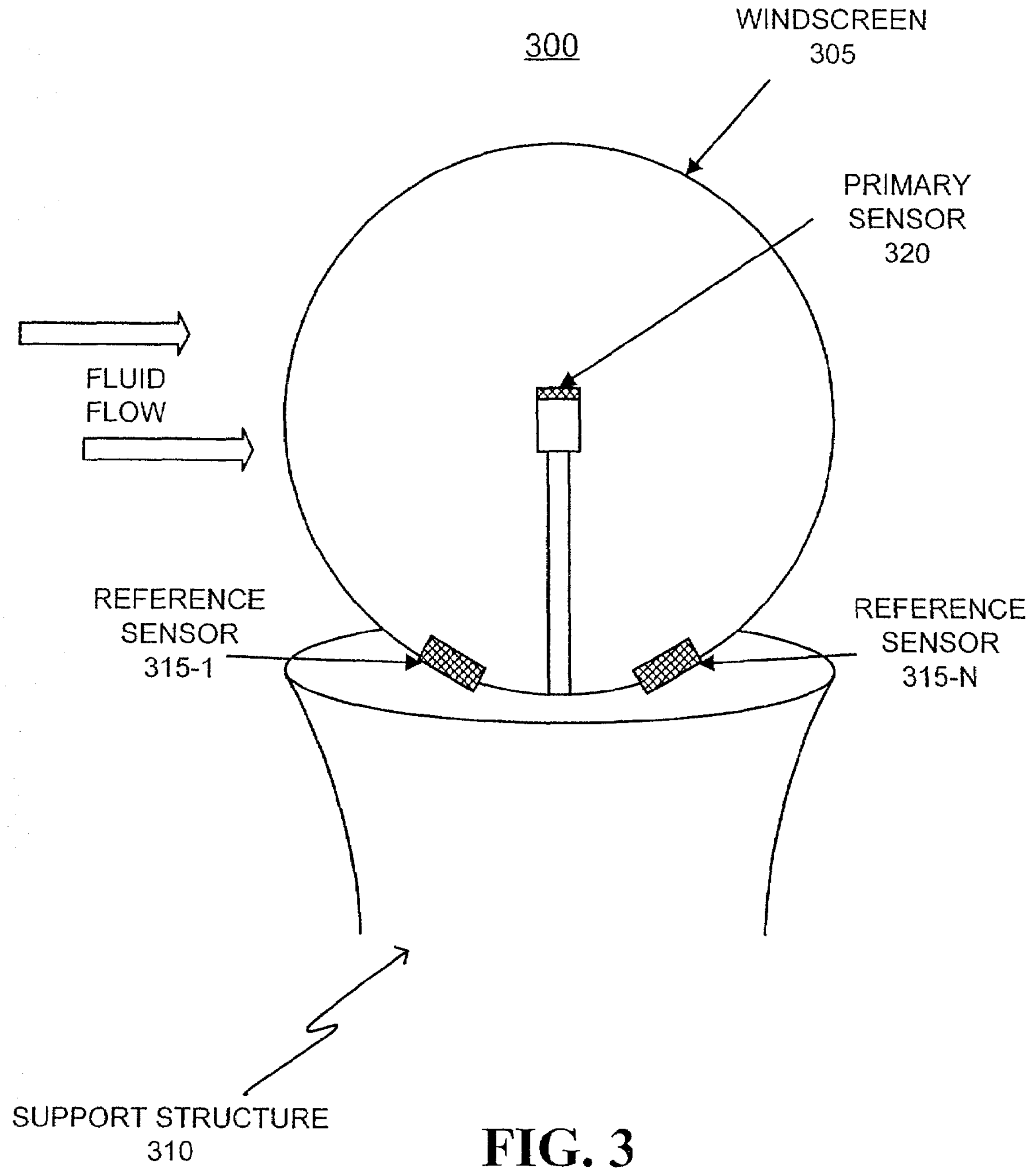
FIG. 3 illustrates another exemplary multi-sensor assembly consistent with the present invention.

FIG. 3 illustrates another exemplary multi-sensor assembly 300 consistent with the present invention. Multi-sensor assembly 300 may include a windscreen 305 coupled to a support structure 310. As illustrated, windscreen 305 may be configured as a three dimensional sphere. Windscreen 305 may be constructed of materials similar to those described above with respect to the exemplary multi-sensor assembly of FIG. 1. Multiple reference sensors (reference sensor 315-1 through reference sensor 315-N) may be distributed on a surface of windscreen 305 so as to couple windscreen 305 to support structure 310. Movement of windscreen 305 due to fluid pressure against a surface of the windscreen, thus, induces signals in one or more of reference sensors 315-1 through 315-N as force from the fluid pressure is coupled from windscreen 305, through the reference sensors, and onto support structure 310. Multi-sensor assembly 300 may additionally include a primary sensor 320 positioned within the approximate center of windscreen 305.

Exemplary Active Noise Cancellation System

Figure 4:
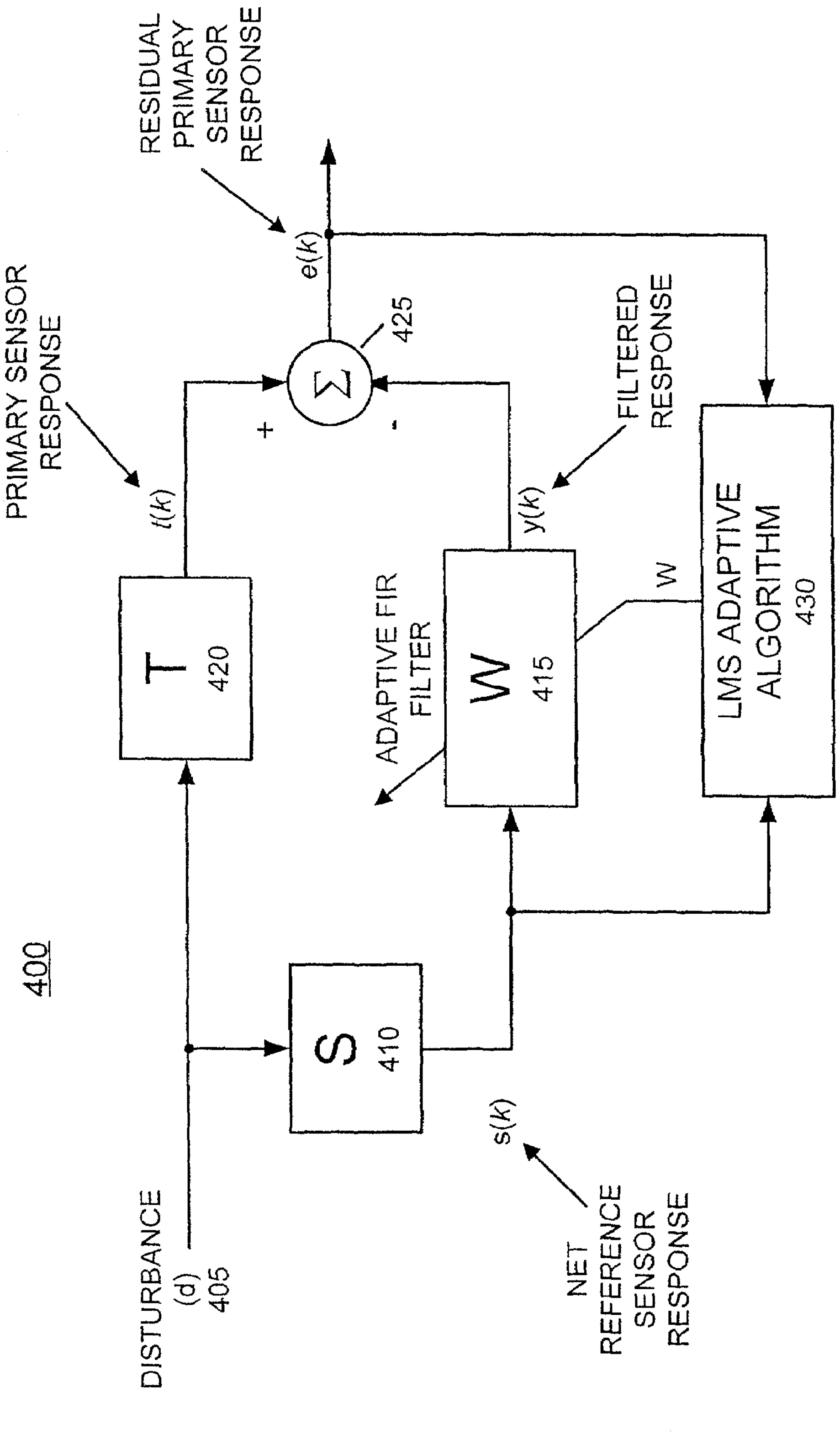
FIG. 4 illustrates an exemplary noise cancellation system consistent with the present invention.

FIG. 4 illustrates an exemplary system 400 in which systems and methods, consistent with the present invention, may be implemented for actively canceling wind noise sensed at a multi-sensor device, such as multi-sensor assembly 100 or 300. System 400 may be implemented in either software or hardware and may include an adaptive FIR filter 415, a summation unit 425 and a least-means-square (LMS) adaptive algorithm 430 which may be implemented in either software or hardware. Active noise cancellation system 400 may actively cancel disturbances (d) 405 that characterize acoustic and non-acoustic noise impinging on the outer surface of windscreen 105 or 305. The disturbances (d) 405 act through the impulse response system S 410 to produce a net reference sensor response s(k). For example, impulse response system S 410 may form a coherent sum of all reference sensor (e.g., reference sensor 1 115-1 through reference sensor N 115-N) responses. The net reference response s(k) is dominated by non-acoustic noise relative to acoustic noise. A primary sensor response t(k) results from disturbance (d) 405 acting through the impulse response system T 420, which characterizes the action of primary sensor 120 or 320. The action of windscreen 105 or 305 does not completely remove the non-acoustic wind noise from the primary sensor response t(k).

Adaptive finite impulse response (FIR) filter 415 may include a conventional digital FIR filter, and may filter the net reference sensor response s(k) received from reference sensors 115 or 315 to produce a filtered response y(k). The filtered response y(k) may be subtracted from the by primary sensor response t(k), at summation unit 425, to produce a residual primary sensor response e(k). The residual primary sensor response e(k) represents the noise reduced output of system 400. This noise-reduced output may be used in a conventional acoustic detection system (not shown) for detecting, classifying, and tracking objects or targets.

The net reference sensor response s(k) and the residual primary sensor response e(k) may be input to a conventional least-means-square (LMS) adaptive algorithm 430 for adaptively updating filter coefficients of filter 415. The adaptive nature of filter 415 accommodates changing conditions, such as, for example, changing wind speed, temperature, or barometric pressure. The LMS algorithm for updating the filter coefficient vector W may be given by:

$$W(k+1)=W(k)+2*mu*e(k)*S(k) \qquad \text{Eqn. (1)}$$

where W(k) is a vector of filter coefficients at time step k;

mu is an adaptation constant;

e(k) is the residual primary sensor response at time step k; and

S(k) is a vector of net reference sensor input samples at time step k.

For an adaptive FIR filter 415 of N filter coefficients, the vector quantities are:

$$W(k+1)=[w_0 w_1 w_2 \ldots w_{N-1}]^T \qquad \text{Eqn. (2)}$$

$$S(k)=[s(k)s(k-1) \ldots s(k-N+1)]^T \qquad \text{Eqn. (3)}$$

The filter coefficients of vector W are adjusted by the LMS algorithm 430 so as to reduce the remaining non-acoustic noise in the primary sensor response t(k) that is correlated with the net reference sensor response s(k). To accomplish this, the LMS algorithm 430 correlates the residual primary sensor response e(k) with the net reference sensor response s(k). The correlated result is multiplied by the adaptation constant mu and then used to adjust the filter coefficients of adaptive filter 415. The LMS algorithm can be iterated, with the objective being convergence to filter coefficients that minimize the average power in the residual primary sensor response e(k). As one skilled in the art will recognize, the choice of mu determines the rate of convergence for the LMS algorithm, and also determines how well the algorithm tracks the optimum solution (i.e., minimum mean-square error) under steady-state conditions. One skilled in the art may choose an appropriate value of mu to achieve a desired tradeoff between a rate of convergence for the LMS algorithm and minimization of mean-square error.

Figure 5:
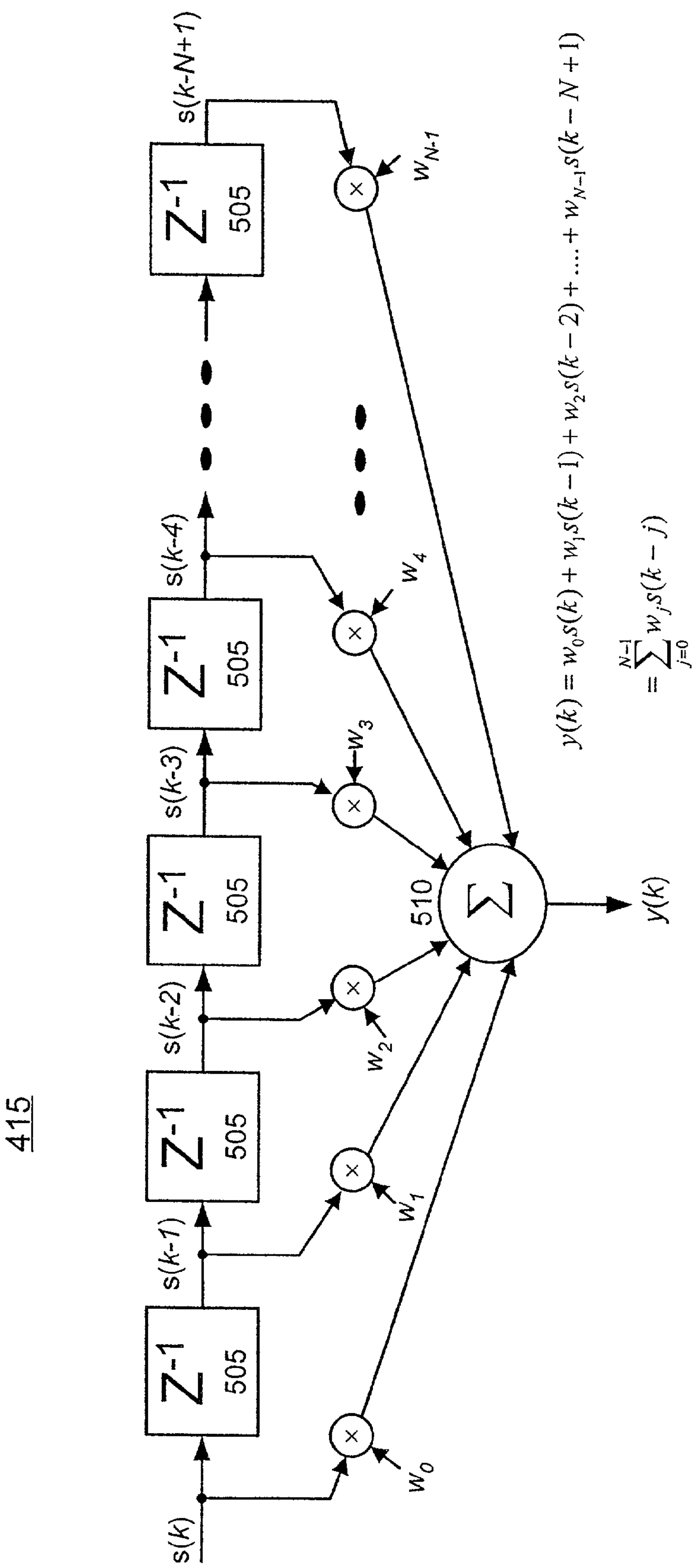
FIG. 5 illustrates an exemplary adaptive finite impulse response (FIR) filter consistent with the present invention.

FIG. 5 illustrates exemplary components of adaptive FIR filter 415. Filter 415 may produce a filtered response y(k) that may include the weighted sum of the current, and past, net reference sensor response s(k) inputs. Filter 415 may include multiple delay elements ($Z^{-1}$) 505 and a summation unit 510 for filtering the net reference sensor response s(k) according to filter coefficients $\{w_0, w_1, w_2 \ldots, w_{N-1}\}$ that are adaptively updated by LMS algorithm 430. As shown, the net reference sensor response s(k) may be successively delayed by each delay element 505 of filter 415. Before and after each delay element 505, a filter coefficient w may be multiplied by the delayed net reference sensor response s(k). The weighted current, and past, net reference sensor inputs may then be summed by summation unit 510. The filtered response y(k) from filter 415, thus, may correspond to the following:

$$y(k)=w_0 s(k)+w_1 s(k-1)+w_2 s(k-2)+ \ldots +w_N s(k-N+1) \qquad \text{Eqn. (4)}$$

$$y(k) = w_0 s(k) + w_1 s(k-1) + w_2 s(k-2) + \ldots + w_N s(k-N+1) \qquad \text{Eqn. (4)}$$

-continued $$= \sum_{j=0}^{N-1} w_j s(k-j) \qquad \text{Eqn. (5)}$$

Exemplary Adaptive Wind Cancellation Process

Figure 6:
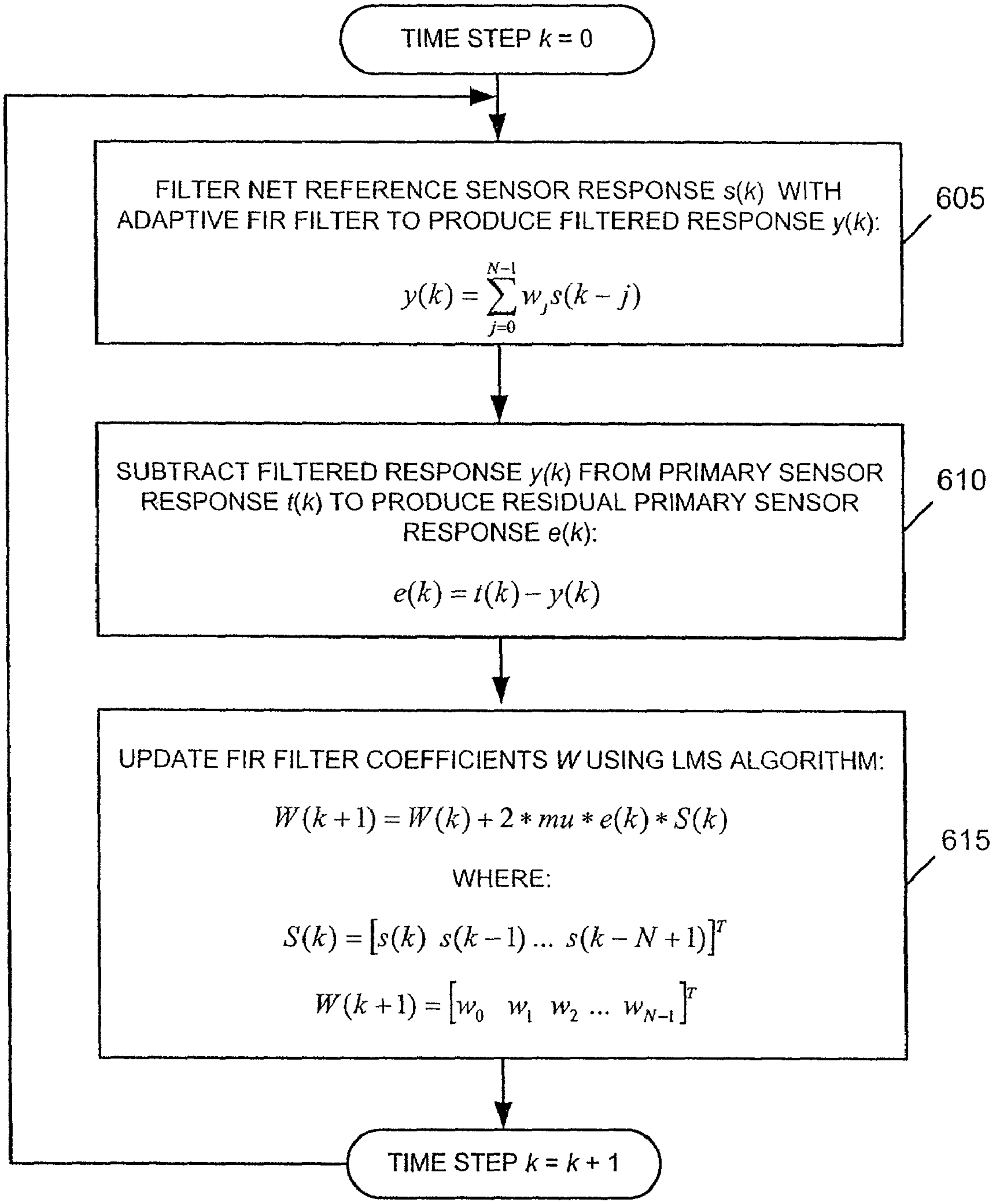
FIG. 6 is a flowchart that illustrates an exemplary process for wind noise cancellation consistent with the present invention.

FIG. 6 illustrates an exemplary process, consistent with the present invention, for canceling wind noise contained in signals received from multiple sensors, such as the sensors of multi-sensor assembly 100 or 300. The exemplary process may begin, at time step k=0, with the filtering of the net reference sensor response s(k) using adaptive FIR filter 415. Filter 415 may produce the filtered response y(k) [act 605] according to Eqn. (5) above. The filtered response y(k) may then be subtracted from the primary sensor response t(k) to produce the residual primary sensor response e(k) [act 610]:

$$e(k)=t(k)-y(k) \qquad \text{Eqn. (6)}$$

Summation unit 425 may, for example, be used to subtract the filtered response y(k) from the primary sensor response t(k) to generate the residual primary sensor response e(k). e(k), as described previously, represents the noise reduced output of system 400 and may be used in acoustic detection systems. The FIR filter 415 coefficients W may then be updated using LMS adaptive algorithm 430 [act 615]. For example, the LMS algorithm of Eqns. (1), (2) and (3) above may be used. At time step k=k+1, the process may return to act 605.

CONCLUSION

Systems and methods, consistent with the present invention, provide mechanisms that enable the detection of a desired acoustic signal incident at a multi-sensor windscreen assembly while reducing wind noise. The multi-sensor windscreen assembly may include multiple sensors distributed across a surface of a three dimensional windscreen, such as a sphere, cylinder, or cone, and may produce a response signal that corresponds to a net pressure acting on the three dimensional body. A primary sensor may further be located within the three dimensional body to sense acoustic pressure signals and non-acoustic pressure disturbances (e.g., wind noise). A finite impulse response (FIR) filter may adaptively filter the response signal from the multiple reference sensors to produce a filtered response. The filtered response may, in turn, be subtracted from a signal from the primary sensor to produce a signal that contains reduced non-acoustic disturbances. The filter may employ a least-means-square (LMS) algorithm for adjusting coefficients of the FIR filter to reduce non-acoustic pressure disturbances, thus, canceling wind noise from an acoustic signal so as to improve the performance of acoustic detection systems.

The foregoing description of exemplary embodiments of the present invention provides illustration and description, but is not intended to be exhaustive or to limit the invention to the precise form disclosed. Modifications and variations are possible in light of the above teachings or may be acquired from practice of the invention. For example, while certain components of the invention have been described as implemented in hardware and others in software, other configurations may be possible. Also, while series of acts have been described with regard to FIG. 6, the order of the acts may be altered in other implementations. No element, step, or instruction used in the description of the present application should be construed as critical or essential to the invention unless explicitly described as such. The scope of the invention is defined by the following claims and their equivalents.

What is claimed is:

1. A method, comprising:

disposing a plurality of secondary sensors on an exterior surface of a three dimensional windscreen;

disposing a primary sensor within an interior of the three dimensional windscreen;

measuring pressure at the primary sensor to produce a primary pressure signal;

measuring pressure at the plurality of secondary sensors to produce secondary pressure signals;

filtering the secondary pressure signals to produce a filtered pressure signal; and subtracting the filtered pressure signal from the primary pressure signal to reduce noise, induced by non-acoustic pressure disturbances, in the primary pressure signal.

2. The method of claim 1, wherein filtering the secondary pressure signals comprises employing a finite impulse response (FIR) filter.

3. The method of claim 2, wherein filtering the secondary pressure signals further comprises using the following relation:

$$y(k)=w_0s(k)+w_1s(k-1)+w_2s(k-2)+ \ldots +w_{N-1}s(k-N-1)$$

wherein N comprises a number of filter coefficients of the FIR filter, k comprises a time step, $\{w_0, w_1, \ldots, w_{N-1}\}$ comprise filter coefficients of the FIR filter, s corresponds to the secondary pressure signals, and y comprises the filtered pressure signal.

4. The method of claim 3, further comprising:

updating the filter coefficients of the FIR filter according to an adaptive algorithm.

5. The system of claim 4, wherein the adaptive algorithm comprises a least-means-square (LMS) algorithm.

6. The method of claim 5, further comprising:

updating the filter coefficients according to the relation:

$$W(k+1)=W(k)+2*mu*e(k)*S(k)$$

wherein $S(k)=[s(k)\ s(k-1) \ldots s(k-N+1)]^T$, $W(k+1)=[w_0\ w_1\ w_2 \ldots w_{N-1}]^T$, mu comprises an adaptation constant, and e comprises the filtered pressure signal subtracted from the primary pressure signal.

7. A system, comprising:

a three dimensional windscreen having an exterior surface and an interior;

a primary sensor located within the interior of the windscreen and configured to measure pressure and to produce a primary pressure signal;

a plurality of secondary sensors disposed on the exterior surface of the windscreen and configured to measure pressure and to produce secondary pressure signals;

a filter configured to process the secondary pressure signals to produce a filtered pressure signal; and a summation unit configured to subtract the filtered pressure signal from the primary pressure signal to reduce noise, induced by non-acoustic pressure disturbances, in the primary pressure signal.

8. The system of claim 7, wherein the filter comprises a finite impulse response (FIR) filter.

9. The system of claim 8, the filter configured to process the secondary pressure signals according to the following relation:

$$y(k)=w_0s(k)+w_1s(k-1)+w_2s(k-2)+ \ldots +w_{N-1}s(k-N-1)$$

wherein N comprises a number of filter coefficients of the FIR filter, k comprises a time step, $\{w_0, w_1, \ldots, w_{N-1}\}$comprise filter coefficients of the FIR filter, s corresponds to the secondary pressure signals, and y comprises the filtered pressure signal.

10. The system of claim 9, further comprising:

updating the filter coefficients of the FIR filter according to an adaptive algorithm.

11. The system of claim 10, wherein the adaptive algorithm comprises a least-means-square (LMS) algorithm.

12. The system of claim 11, wherein the LMS algorithm updates the filter coefficients according to the relation:

$$W(k+1)=W(k)+2*mu*e(k)*S(k)$$

wherein $S(k)=[s(k)\ s(k-1) \ldots s(k-N+1)]^T$, $W(k+1)=[w_0\ w_1\ w_2 \ldots w_{N-1}]^T$, mu comprises an adaptation constant, and e comprises the filtered pressure signal subtracted from the primary pressure signal.

13. A method, comprising:

disposing a plurality of second sensors on an exterior surface of a three dimensional windscreen; disposing a first sensor within an interior of the three dimensional windscreen;

sensing disturbances at the first sensor and the plurality of second sensors, the first sensor producing a first signal and the plurality of second sensors producing second signals;

adaptively filtering the second signals to produce a filtered signal; and subtracting the filtered signal from the first signal to cancel the disturbances associated with the first signal.

14. The method of claim 13, wherein adaptively filtering the first signal comprises using a digital filter.

15. The method of claim 14, wherein the digital filter comprises a plurality of filter coefficients.

16. The method of claim 15, wherein adaptively filtering the first signal second signals comprises:

adjusting the adaptive filtering according to a least-means-square algorithm.

17. A system for canceling disturbances from a sensor signal, comprising:

a first sensor and a plurality of second sensors configured to sense disturbances, the first sensor producing a first signal and the plurality of second sensors producing second signals;

a filter configured to adaptively filter the second signals to produce a filtered signal;

a summation unit configured to subtract the filtered signal from the first signal to cancel the disturbances from the first signal; and a windscreen, wherein the first sensor is disposed within an interior of the windscreen and wherein the plurality of second sensors are disposed on an external surface of the windscreen.

18. The system of claim 17, wherein the filter comprises a digital filter.

19. The system of claim 18, wherein the digital filter comprises a plurality of filter coefficients.

20. The system of claim 19, the filter being further configured to:

update the filter coefficients according to a least-means-square algorithm.

21. A method, comprising:

measuring pressure with a first sensor located inside a windscreen to produce a measurement signal;

measuring pressure at a plurality of second sensors disposed on an exterior surface of the windscreen to infer a net pressure acting on the windscreen, the net pressure comprising acoustic and non-acoustic pressure;

filtering signals from the plurality of second sensors to estimate a component of the non-acoustic pressure that is correlated with the net pressure; and subtracting the estimated component of non-acoustic pressure from the measurement signal to reduce noise in the measurement signal.

* * * * *